(12) United States Patent
Smirnov et al.

(10) Patent No.: US 9,285,687 B2
(45) Date of Patent: Mar. 15, 2016

(54) INSPECTION APPARATUS, LITHOGRAPHIC APPARATUS, AND DEVICE MANUFACTURING METHOD

(75) Inventors: Stanislav Y Smirnov, Danbury, CT (US); Lev Ryzhikov, Norwalk, CT (US); Eric Brian Catey, Danbury, CT (US); Adel Joobeur, Milford, CT (US); David Heald, Brookfield, CT (US); Yevgeniy Konstantinovich Shmarev, Lagrangeville, NY (US); Richard Jacobs, Brookfield, CT (US)

(73) Assignee: ASML Holding N.V., Veldhoven (NL)

( * ) Notice: Subject to any disclaimer, the term of this patent is extended or adjusted under 35 U.S.C. 154(b) by 599 days.

(21) Appl. No.: 13/608,069

(22) Filed: Sep. 10, 2012

(65) Prior Publication Data

US 2013/0083306 A1    Apr. 4, 2013

Related U.S. Application Data

(60) Provisional application No. 61/542,440, filed on Oct. 3, 2011, provisional application No. 61/546,273, filed on Oct. 12, 2011, provisional application No. 61/553,458, filed on Oct. 31, 2011.

(51) Int. Cl.
*G03F 7/20* (2006.01)

(52) U.S. Cl.
CPC ........ *G03F 7/70625* (2013.01); *G03F 7/70633* (2013.01)

(58) Field of Classification Search
CPC .......... G01J 3/447; G01J 4/00; G01N 21/211; G01N 21/274; G01N 2021/213; G01N 21/47; G03F 7/70633; G03F 7/70625; G03F 7/7063; G02B 17/0808; G02B 17/0856; G02B 27/0025
See application file for complete search history.

(56) References Cited

U.S. PATENT DOCUMENTS

| 5,444,573 A | 8/1995 | Saito |
|---|---|---|
| 6,501,603 B2 | 12/2002 | Kasahara |

(Continued)

FOREIGN PATENT DOCUMENTS

| CN | 101587306 A | 11/2009 |
|---|---|---|
| CN | 101939857 A | 1/2011 |

(Continued)

OTHER PUBLICATIONS

"Multiple Target Metrology," Research Disclosure Database No. 569030, Questel Ireland, Ltd., 2011; 4 pages.
English-Language Abstract for Japanese Patent Publication No. 2009-037060 A, published Feb. 19, 2009; 1 page.

(Continued)

*Primary Examiner* — Mesfin T Asfaw
(74) *Attorney, Agent, or Firm* — Sterne, Kessler, Goldstein & Fox P.L.L.C.

(57) ABSTRACT

An inspection apparatus includes an illumination system that receives a first beam and produces second and third beams from the first beam and a catadioptric objective that directs the second beam to reflect from a wafer. A first sensor detects a first image created by the reflected second beam. A refractive objective directs the third beam to reflect from the wafer, and a second sensor detects a second image created by the reflected third beam. The first and second images can be used for CD measurements. The second beam can have a spectral range from about 200 nm to about 425 nm, and the third beam can have a spectral range from about 425 nm to about 850 nm. A third sensor may be provide that detects a third image created by the third beam reflected from the wafer. The third image can be used for OV measurements.

21 Claims, 13 Drawing Sheets

(56) References Cited

U.S. PATENT DOCUMENTS

| | | |
|---|---|---|
| 6,603,529 B1 | 8/2003 | Finarov |
| 7,050,223 B1 | 5/2006 | Hoppen |
| 7,633,689 B2 | 12/2009 | Shmarev et al. |
| 8,491,816 B2 | 7/2013 | Hong et al. |
| 2004/0235205 A1 | 11/2004 | Levy et al. |
| 2007/0182964 A1 | 8/2007 | Den Boef et al. |
| 2008/0049226 A1 | 2/2008 | Mieher et al. |
| 2008/0279442 A1 | 11/2008 | Den Boef et al. |
| 2009/0021845 A1* | 1/2009 | Shmarev et al. ............. 359/730 |
| 2010/0231884 A1 | 9/2010 | Mann |
| 2011/0027704 A1 | 2/2011 | Cramer et al. |

FOREIGN PATENT DOCUMENTS

| | | |
|---|---|---|
| DE | 10 2007 051 669 A1 | 4/2009 |
| EP | 1 628 164 A2 | 2/2006 |
| EP | 2 219 078 A1 | 8/2010 |
| JP | 2009-037060 A | 2/2009 |
| WO | WO 2010/069757 A1 | 6/2010 |
| WO | WO 2011/045132 A1 | 4/2011 |

OTHER PUBLICATIONS

English-Language Abstract for Chinese Patent Publication No. 101587306 A, published Nov. 25, 2009; 1 page.

* cited by examiner

INSPECTION APPARATUS, LITHOGRAPHIC APPARATUS, AND DEVICE MANUFACTURING METHOD

CROSS-REFERENCE TO RELATED APPLICATIONS

This application claims benefit under 35 U.S.C. §119(e) to U.S. Provisional Patent Application No. 61/542,440, filed Oct. 3, 2011; U.S. Provisional Patent Application No. 61/546,273, filed Oct. 12, 2011; and U.S. Provisional Patent Application No. 61/553,458, filed Oct. 31, 2011, which are all incorporated by reference herein in their entireties.

BACKGROUND

1. Field

The present invention relates to an inspection apparatus usable, for example, in the manufacture of devices by lithographic techniques.

2. Related Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between two layers formed in or on the patterned substrate and critical line width of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-destructive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

With the further shrinking of resist thickness and the introduction of more complicated lithographic stacks (e.g., stacks configured for double exposure), critical dimension (CD) and overlay (OV) metrology performance will also have to improve to monitor the lithographic processes. One way to improve CD metrology performance is to reduce the wavelength of the measurement radiation, for example, ultraviolet radiation. However, OV metrology often requires radiation having near-infrared wavelengths to view overlay targets through different process layers. Accordingly, there is a need for inspection apparatuses, such as scatterometers, that can operate within a spectral band from about 200 nm to about 850 nm to make both CD and OV measurements without compromising optical performance regarding, for example, field of view, pupil aberrations, over all transmission, polarization properties (induced ellipticity), and transmission uniformity. Reduced optical performance can lead to reduced accuracy of the OV and CD measurements, as well as reduced system productivity.

Another way to improve CD and OV metrology performance is to improve the objectives used with inspection apparatuses. There are two types of objectives generally used for scatterometry applications: refractive objectives and catadioptric objectives. One disadvantage of previous refractive objectives is that the working distance is relatively small. For example, the working distance is generally less than 0.35 mm when the numerical aperture (NA) equals about 0.95. Another disadvantage of previous refractive objectives is that the operational wavelength spectral range is limited to about 450-700 nm. Further, previous refractive objectives only have plan apochromatic aberration correction. Accordingly, there is a need for a refractive objective having an increased working distance, an increased operational spectral bandwidth, and improved apochromatic aberration correction.

One disadvantage of previous catadioptric objectives is that they induce field curvature—previous catadioptric objectives typically have a large Petzval sum that is far from zero. Previous catadioptric objectives also suffer from obscuration that decreases image contrast. Catadioptric objectives for an inspection apparatus such as a scatterometer can also be corrected for pupil aberrations. Pupil aberrations in the previous catadioptric objectives are large because of large Petzval curvature and pupil size.

SUMMARY

Accordingly, there is a need for improved inspection apparatuses, catadioptric objectives, and refractive objectives.

In one embodiment, an inspection apparatus includes an illumination system configured to receive a first beam and to produce second and third beams from the first beam, and a catadioptric objective configured to direct the second beam to reflect from a wafer. The inspection apparatus includes a first sensor configured to detect a first image created by the reflected second beam. The inspection apparatus also includes a refractive objective configured to direct the third beam to reflect from the wafer, and a second sensor configured to detect a second image created by the reflected third beam. In one embodiment, the first and second images can be used for CD measurements. In one embodiment, the second beam has a spectral range from about 200 nm to about 425 nm, and the third beam has a spectral range from about 425 nm to about 850 nm. The inspection apparatus can also include a third sensor configured to detect a third image created by the third beam reflected from the wafer. In one embodiment, the third image can be used for OV measurements.

In another embodiment, a refractive objective, for example, a refractive objective that can be used with an inspection apparatus, has a front lens group, a middle lens group, and a back lens group. The front lens group includes front and back meniscus lenses. The middle lens group includes a first doublet, a second doublet, a triplet, and a doublet in order from a front to a back of the refractive objective. The back lens group includes a negative doublet.

In another embodiment, an objective system, for example, an objective system that can be used with an inspection apparatus, includes a catadioptric objective and at least two mirrors configured to reduce field curvature induced by the catadioptric objective.

In one embodiment, a lithographic apparatus includes an illumination optical system arranged to illuminate a pattern, a projection optical system arranged to project an image of the pattern onto a substrate, and an inspection apparatus. The inspection includes an illumination system configured to receive a first beam and to produce second and third beams from the first beam, and a catadioptric objective configured to direct the second beam to reflect from a wafer. The inspection apparatus includes a first sensor configured to detect a first image created by the reflected second beam. The inspection apparatus also includes a refractive objective configured to direct the third beam to reflect from the wafer, and a second sensor configured to detect a second image created by the reflected third beam.

In another embodiment, a method of determining substrate parameters includes directing a first beam through a catadioptric objective onto the substrate such that the first beam reflects from the substrate, and forming a first image of the substrate using the reflected first beam. A first parameter of the substrate can be determined using the first image. The method also includes directing a second beam through a refractive objective onto the substrate such that the second beam reflects from the substrate, and forming a second image of the substrate using the reflected second beam. A second parameter of the substrate can be determined using the second image.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate embodiments of the present invention and, together with the description, further serve to explain the principles of the invention and to enable a person skilled in the relevant art(s) to make and use the invention.

FIG. 1 depicts a lithographic apparatus.
FIG. 2 depicts a lithographic cell or cluster.
FIG. 3 depicts a first scatterometer.
FIG. 4 depicts a second scatterometer.
FIG. 5 depicts an inspection apparatus according to an embodiment.

Figure 1:
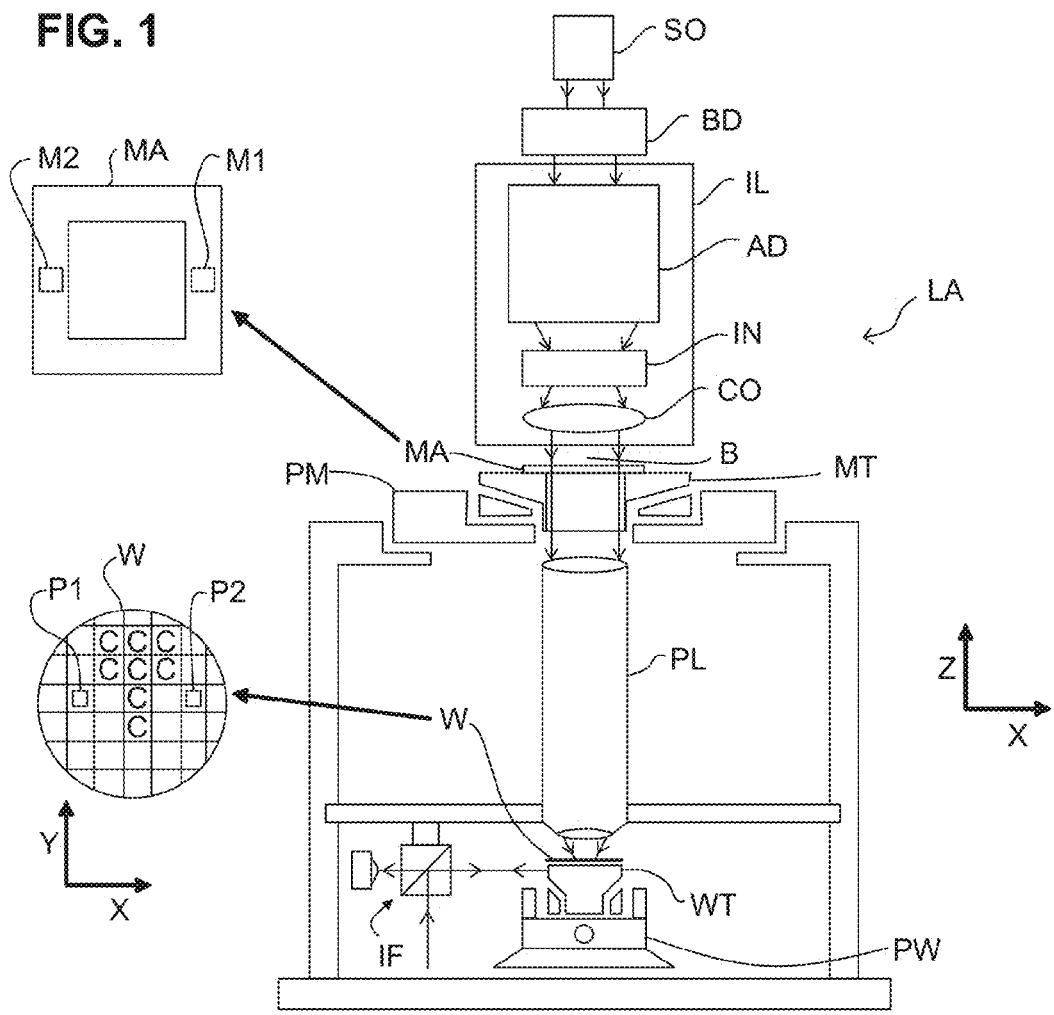

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Before describing such embodiments in more detail, however, it is instructive to present an example environment in which embodiments of the present invention may be implemented.

FIG. 1 schematically depicts a lithographic apparatus. The apparatus comprises an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
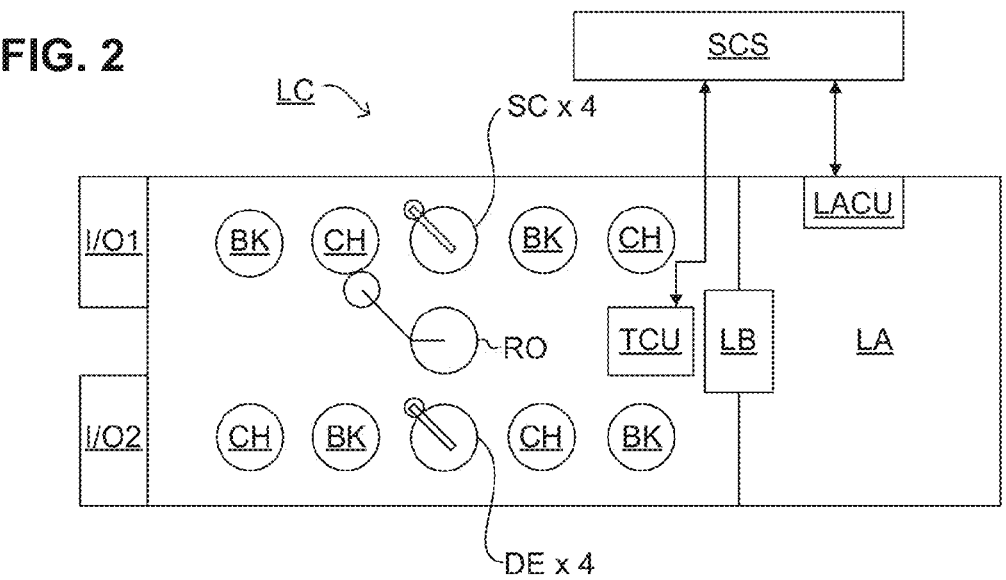

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between two layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
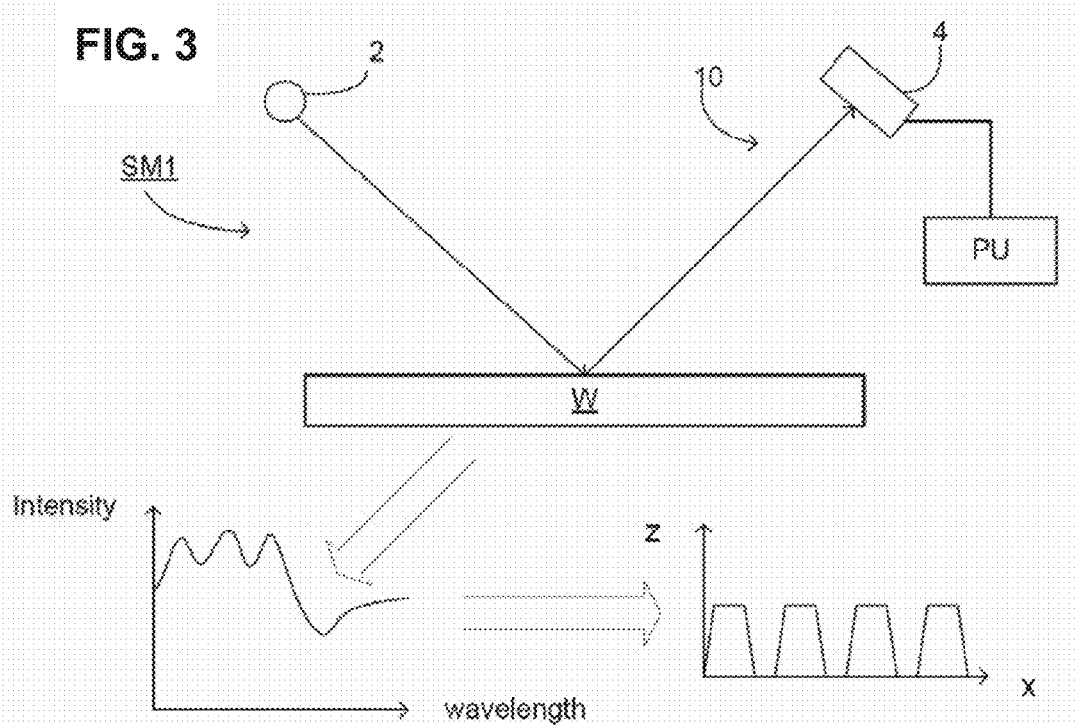

FIG. 3 depicts a scatterometer which may be used in some embodiments of the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer. At normal incidence, however, this scatterometer has no sensitivity for pattern asymmetry. In order to detect pattern asymmetry in the 0-th diffraction order, oblique incidence is needed.

Figure 4:
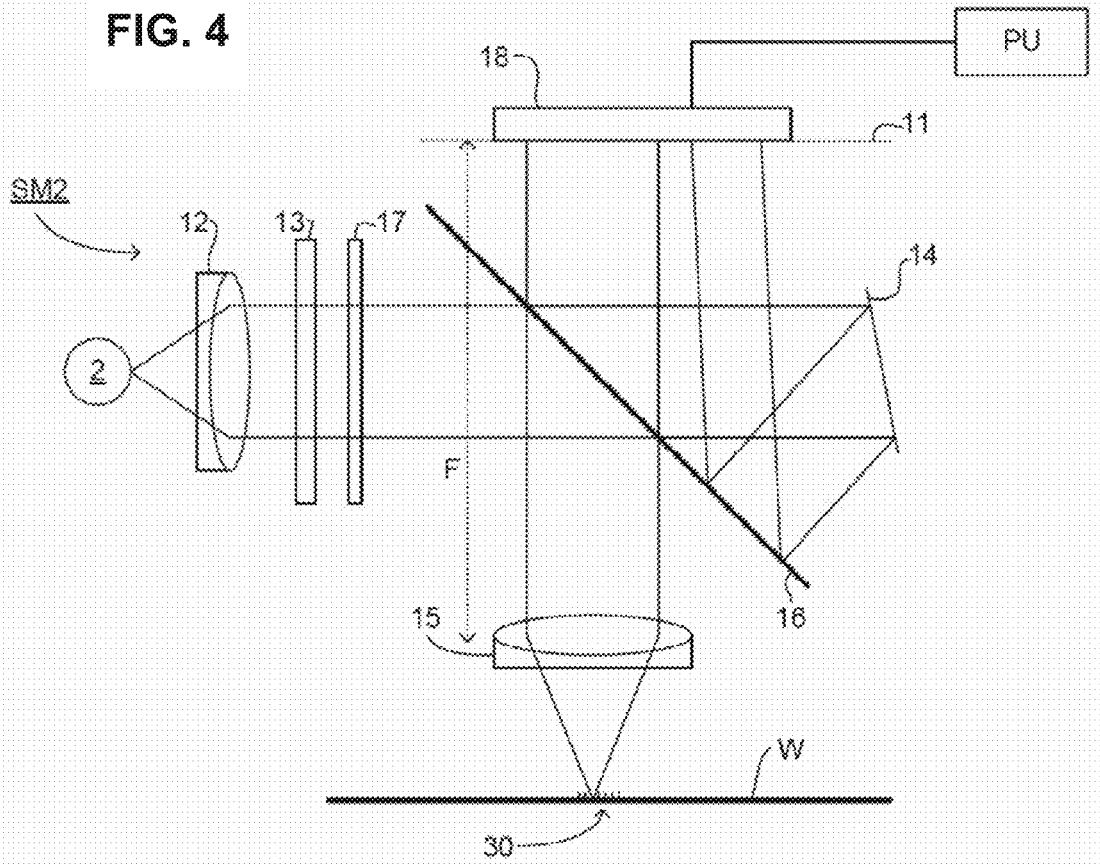

Another scatterometer that can be used in some embodiments is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), in some embodiments, at least 0.9, and in some embodiments, at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

The target 30 on substrate W may be a 1-D periodic grating, which is printed such that after development, the bars are formed of solid resist lines. The target 30 may be a 2-D periodic grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Figure 5:
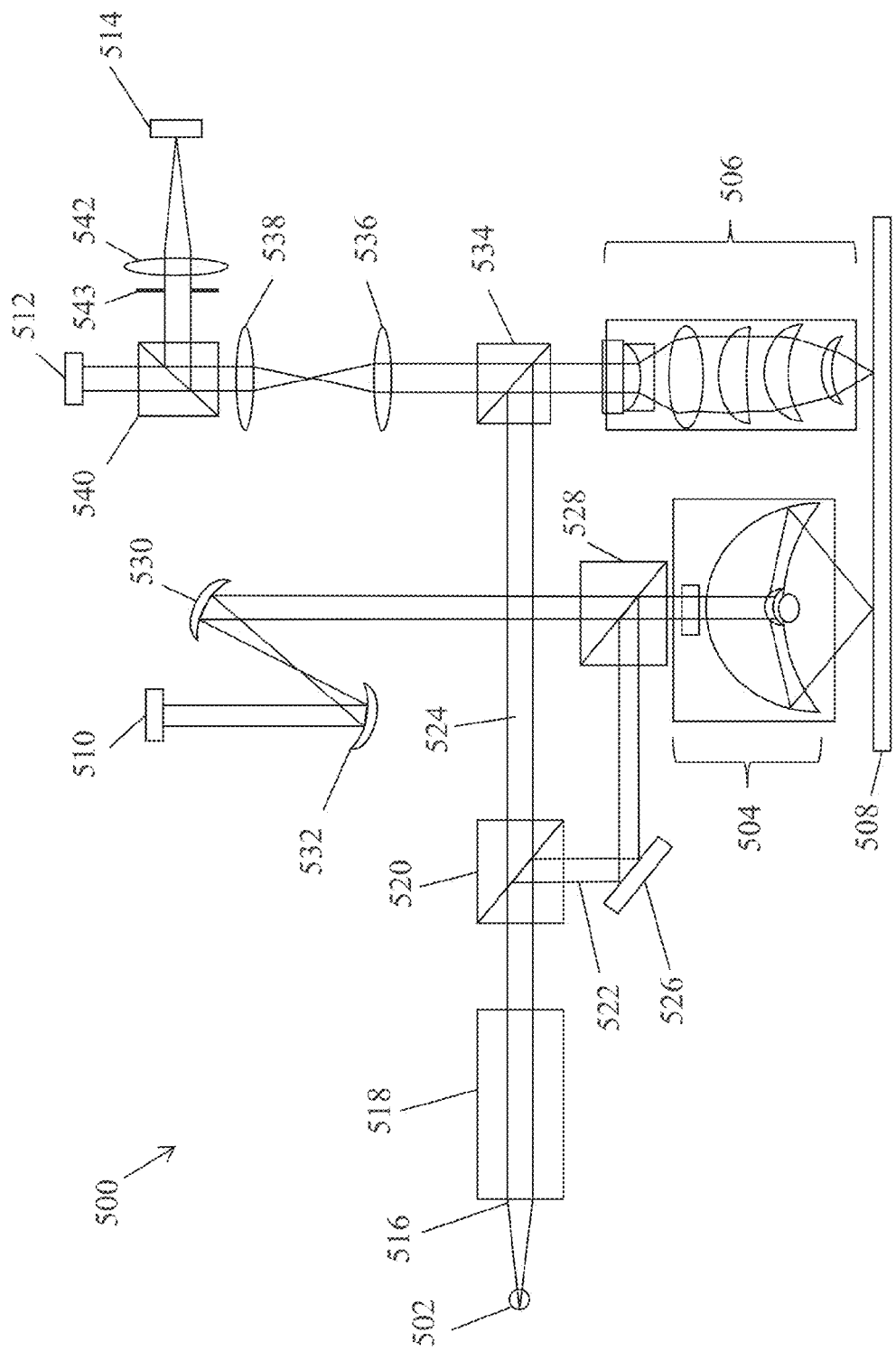

FIG. 5 depicts an inspection apparatus 500 according to an embodiment. Inspection apparatus 500 can be a scatterometry system. Scatterometry system 500 can sense one or more properties, such as CD and OV measurements, of a wafer 508. In one embodiment, inspection apparatus 500 operates in a wide spectral range from about 200 nm to about 850 nm. Inspection apparatus 500 can be used in EUV lithography and allows for high productivity and accurate CD and OV metrology.

Inspection apparatus 500 includes a radiation source 502, a catadioptric objective 504, a refractive objective 506, a first sensor 510, and a second sensor 512. Radiation source 502 can be, for example, a broadband (white light) radiation source. Radiation source 502 produces a radiation beam 516. Inspection apparatus 500 may also include an illuminator 518 that is configured to condition radiation beam 516. One example of an illuminator that can be used with inspection apparatus 500 is further described below with reference to FIG. 16.

In one example, apparatus 500 produces first and second beams 522 and 524 from source radiation beam 516. Apparatus 500 is configured to direct first beam 522 to catadioptric objective 504. Apparatus 500 is configured to direct second beam 524 to refractive objective 506. In one embodiment, first beam 522 has a spectral range from about 200 nm to about 425 nm, and second beam 524 has a spectral range from about 425 nm to about 850 nm.

In one embodiment, apparatus 500 includes an illumination system including illuminator 518 and a beam splitter 520 that splits beam 516 into first beam 522 and second beam 524. Beam splitter 520 can be two triangular prisms or any other optical device configured to split radiation beam 516 into first beam 522 and second beam 524.

In another embodiment, apparatus 500 includes a switchable mirror device (not shown) that is configured to re-direct radiation beam 516 between an optical path directed to catadioptric objective 504 and an optical path directed to refractive objective 506.

In one example, within the optical path to catadioptric objective 504 apparatus 500 may also include one or more fold mirrors or one or more beam splitters configured to direct first beam 522 to catadioptric objective 504. In the example shown in FIG. 5, apparatus 500 includes one fold mirror 526 and one beam splitter 528 that directs beam 522 from beam splitter 520 to catadioptric objective 504.

First beam 522 is directed through catadioptric objective 504 and focused on a portion of wafer 508. First beam 522 is then reflected back through catadioptric objective 504 and beam splitter 528, and directed to first sensor 510.

Catadioptric objective 504 can have a large NA. For example, catadioptric objective 504 can have an NA that ranges from about 0.90 to about 1.0, and in some embodiments, an NA of about 0.95. Catadioptric objective 504 can also be achromatic over a wide spectral range, for example, a range from about 200 nm to about 425 nm. In some embodiments, catadioptric objective 504 improves the coating and transmission properties of the optical system. In other embodiments, catadioptric objective 504 is a robust monolithic, two element design as further described below with reference to FIG. 8.

Apparatus 500 may also include one or more relay mirrors configured to direct first beam 522 from catadioptric objective 504 to first sensor 510. As shown in FIG. 5, apparatus 500 includes a first relay mirror 530 and a second relay mirror 532 that are configured to direct first beam 522 from beam splitter 528 to first sensor 510.

The image formed on first sensor 510 is used to determine one or more characteristics of wafer 508. First sensor 510 can be a charge coupled device (CCD) or any other suitable image sensing device. First sensor 510 can be used for CD measurements or large target OV measurements.

Figure 6:
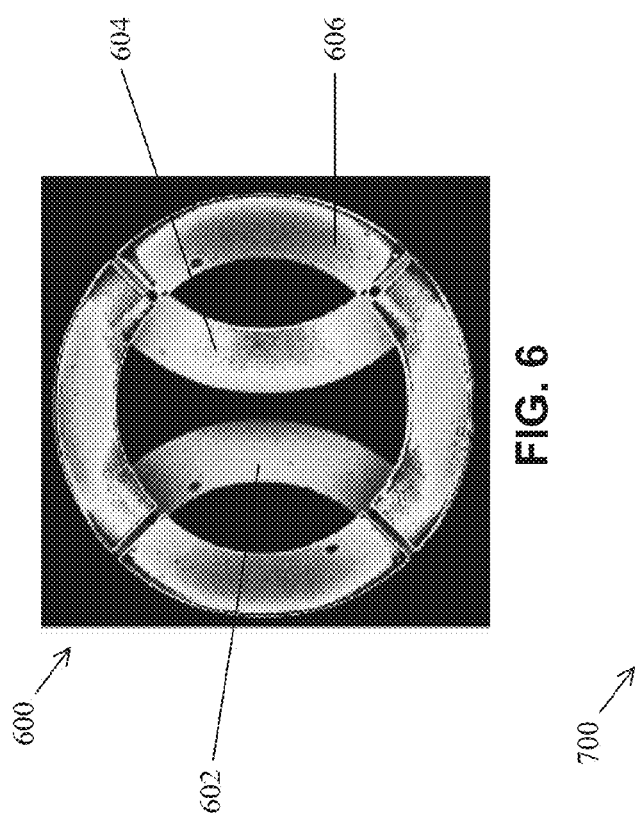
FIG. 6 illustrates an image formed on a sensor of the inspection apparatus of FIG. 5 that is used for CD measurements.

FIG. 6 illustrates an exemplary pupil image 600 formed on first sensor 510 when using an annular aperture. Using an annular aperture separates out the different diffraction orders such that the zero diffraction order 606, the −1st diffraction order 602, and the +1st diffraction order 604 are superposed as shown in FIG. 6. The pupil aperture can have shapes other than an annulus based on the application, for example, the pupil aperture can be a circle, segment, dipole, slit, or any other suitable shape Annular apertures are generally used for CD measurements and OV measurements on large targets.

Apparatus 500 may also include one or more optical elements configured to direct second beam 524 to refractive objective 506. As shown in FIG. 5, apparatus 500 includes a beam splitter 534 that directs beam 524 from beam splitter 520 to refractive objective 506. Refractive objective 506 can be any suitable refractive objective. For example, in some embodiments, refractive objective 506 includes one or more optical lenses as discussed in more detail below with reference to FIGS. 13-15.

In one example, second beam 524, which may have a spectral range from about 425 nm to about 850 nm, is directed through refractive objective 506 and focused on a portion of wafer 508. Second beam 524 is then reflected back through refractive objective 506 and beam splitter 534, and directed to second sensor 512. Apparatus 500 may also include one or more optical elements configured to direct and condition second radiation beam 524 to second sensor 512. For example, as shown in FIG. 5, apparatus 500 includes a first relay lens 536 and a second relay lens 538. The reflected second beam 524 is directed to second sensor 512 to form an image. Second sensor 512 can be a CCD or any other suitable sensing device. In one embodiment, a pupil image similar to the pupil image 600 illustrated in FIG. 6 can be formed on second sensor 512 and used for CD measurements and OV measurements on large targets.

In one example, inspection apparatus 500 can also include a third sensor 514. Third sensor 514 can be a CCD or any other suitable sensing device. Third sensor 514 is configured for OV measurements and, particularly, for OV measurements of small targets. As shown in FIG. 5, in this example, apparatus 500 includes a fourth beam splitter 540 that splits second beam 524 reflected from wafer 508 into two beams: one beam is directed to second sensor 512 and the other beam is directed to third sensor 514.

Figure 7:
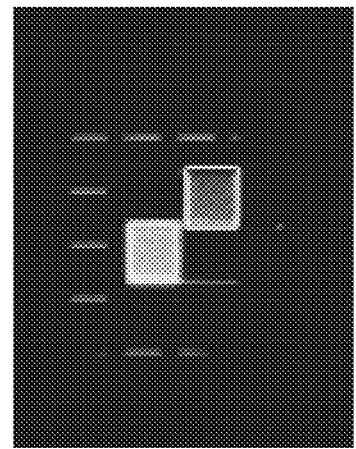
FIG. 7 illustrates an image formed on a sensor of the inspection apparatus of FIG. 5 that is used for OV measurements.

In one example, inspection apparatus 500 includes one or more optical elements between fourth beam splitter 540 and third sensor 514 configured to focus an image sport of the wafer on third sensor 514 for OV measurements. For example, as shown in FIG. 5, inspection apparatus 500 includes a relay lens 542 and a spatial filter or field stop 543 configured for a dark field detection method that blocks the zero diffraction order. An example of this system is described in U.S. Patent Application Publication No. 2011/0027704, filed Jul. 29, 2010, which is incorporated herein by reference in its entirety. FIG. 7 illustrates an exemplary spot image of wafer 508, including wafer marks, formed on third sensor 514. The aperture of field stop 543 blocks the zero diffraction order. Images such as the one shown in FIG. 7 formed on third sensor 514 can be used to determine one or more characteristics of wafer 508, for example, small target OV measurements.

Accordingly, in one example, separating source radiation beam 516 into first radiation beam 522 having a spectral range from about 200 nm to about 425 nm and a second radiation beam having a spectral range from about 425 nm to about 850 nm enhances optical performance. While preserving the wide spectral range of inspection apparatus 500 as a whole.

Because inspection apparatus 500 as shown in FIG. 500 includes one radiation source 502, catadioptric objective 504 and refractive objective 506 have matching parameters, for example, matching pupil sizes, focal distances, and NA, in one embodiment. For example, catadioptric objective 504 and refractive objective 506 can both have a pupil diameter that ranges from about 6.6 mm to about 6.7 mm. The optical pass established between the pupil apertures in illuminator 518 and the pupils in each objective can also be equal.

Example Embodiments of a Catadioptric Objective

Figure 8:
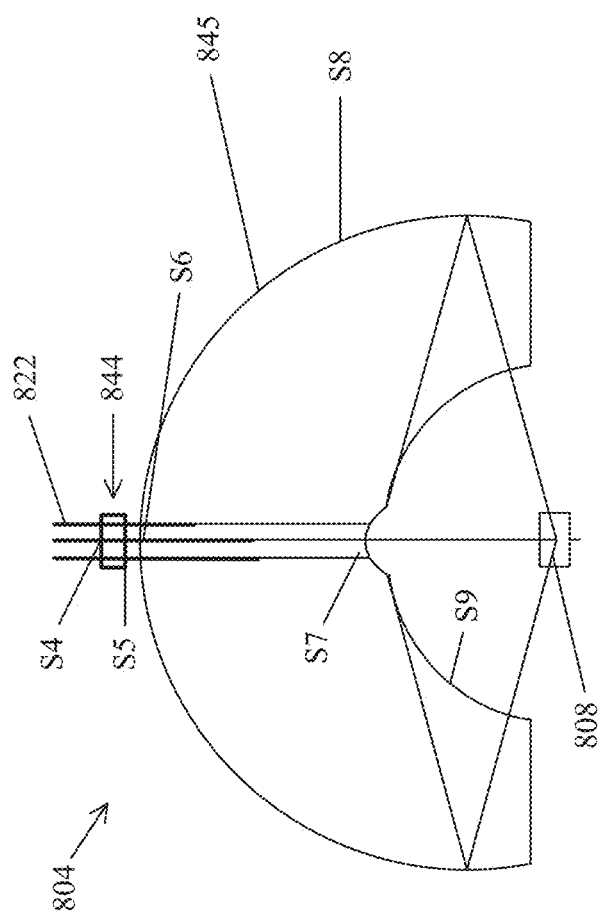
FIG. 8 depicts an optical schematic of a catadioptric objective.

FIG. 8 schematically illustrates a catadioptric objective 804 that can be used with inspection apparatus 500 shown in FIG. 5. As shown in FIG. 8, catadioptric objective 804 includes a refractive element 844 and a monolithic element 845, for example, a monolithic glass element. Refractive element 844 conditions a second radiation beam 822, for example, a radiation beam that was split by beam splitter 520 of apparatus 500 as shown in FIG. 5, having a spectral range from about 200 nm to about 425 nm, to correct one or more optical aberrations (such as coma). As shown in FIG. 8, refractive element 844 includes surfaces S4 and S5. Monolithic element 845 comprises a reflective convex surface S7 that is positioned to reflect radiation beam 822 conditioned by refractive element 844. Monolithic element 845 includes a concave surface S8 that is reflective and a surface S6 that is substantially transparent to light in a desired wavelength range. Transparent surface portion S6 is centered around the optical axis and has a diameter that can be based on the width of radiation beam 822. In one example, surface S6 passes radiation beam 822 coming from refractive element 844, and surface S8 reflects rays of beam 822 coming from surface S7. That is, radiation beam 822 conditioned by refractive element 844 passes through transparent surface S6 of monolithic element 845 and impinges on convex reflective surface S7.

Surface S8 of monolithic element 845 receives the radiation reflected by convex surface S7 and reflects this radiation toward a target portion of a wafer 808. Before impinging on the target portion of wafer 808, the radiation traverses surface S9 of monolithic element 845. In one embodiment, all rays reflecting off of reflective surface S8 exit monolithic element 845 perpendicular to surface S9, and are therefore not refracted by surface S9. As a result, catadioptric objective 804 can be achromatic.

Monolithic element 845 can comprise glass, for example, fused silica ($SiO_2$).

An example prescription for designing the optical surfaces depicted in the embodiment of FIG. 8 is set forth below in Table 1.

TABLE 1

| S # | Surface Type | Radius | Thickness |
|---|---|---|---|
| S1 | Sphere | infinity | infinity |
| S2 | Sphere | infinity | 29.91889 |
| S3 | Sphere | infinity | −29.9189 |
| S4 | Sphere | infinity | 4 |
| S5 | Asphere | 47.16811 | 1.879349 |
| S6 | Asphere | 49.52582 | 36.96539 |
| S7 | Asphere | 4.149334 | −36.9654 |
| S8 | Asphere | 49.52582 | 39.46539 |
| S9 | Sphere | 28.24973 | 28.24973 |

In one embodiment, aspheric surfaces S5, S6, S7, and S8 can be designed according to the following aspheric equation:

$$Z(r) = \frac{cr^2}{1+\sqrt{1-(1+k)c^2r^2}} + Ar^4 + Br^6 + Cr^8 + Dr^{10} + Er^{12} + Fr^{14} + Gr^{16} + Hr^{18} + Jr^{20} \quad \text{(Eq. 1)}$$

wherein $r = x^2 + y^2$;

c is the curvature (1/RDY) of the surface;
k is the conic constant; and
A through J are the aspheric coefficients.

In one embodiment, using Equation 1, aspheric surfaces S5 and S8 can have the parameters set forth below in Table 2.

TABLE 2

|  | s5 | s8 |
|---|---|---|
| Y Radius (RDY) | 47.16811 | 49.52582 |
| Conic Constant (k) | 47.9979 | −0.05977 |
| 4th Order Coefficient (A) | −0.00023 | 1.18E−09 |
| 6th Order Coefficient (B) | 1.80E−06 | −2.66E−13 |
| 8th Order Coefficient (C) | 2.30E−07 | 4.61E−16 |
| 10th Order Coefficient (D) | −1.20E−09 | −3.00E−19 |
| 12th Order Coefficient (E) | 0 | 1.26E−22 |
| 14th Order Coefficient (F) | 0 | −2.96E−26 |
| 16th Order Coefficient (G) | 0 | 3.48E−30 |
| 18th Order Coefficient (H) | 0 | 0 |
| 20th Order Coefficient (J) | 0 | 0 |

In other embodiments, a catadioptric objective used with inspection apparatus 500 as shown in FIG. 5 may include other suitable design forms of catadioptric objectives, for example, the design forms as described in U.S. Pat. No. 7,633,689, which is incorporated herein by reference in its entirety. In some embodiments, a catadioptric objective used with inspection apparatus 500 shown in FIG. 5 can be any catadioptric objective suitable for use with radiation having a spectral range from about 200 nm to about 424 nm.

In some embodiments, a catadioptric objective system used with inspection apparatus 500 can include a catadioptric objective and at least two mirrors to correct the field curvature created by the catadioptric objective. The catadioptric objective used in catadioptric objective systems that correct field curvature can take the form of any of the above-described embodiments or any other suitable form of a catadioptric objective.

The additional mirrors can be configured to correct or reduce the total field curvature of the catadioptric objective system because field curvature depends on the curvature of optical surfaces. Particularly, the reflective surfaces of the mirrors compensate for the effect of, for example, surface S9 as shown in FIG. 8. Each mirror can be either a first surface or a second surface (for example, a Mangin mirror) mirror. Each mirror can have either a spherical or aspherical shape.

In one embodiment, the sum of the average curvatures (A) of the additional mirrors defined at the center of their clear apertures is greater than zero: A>0. For first surface mirrors, curvature is positive for concave surfaces and negative for convex surfaces. For second surface mirrors, curvature is positive for convex surfaces and negative for concave surfaces. When A>0 for the mirrors of the catadioptric objective system, the mirrors induce field curvature having a sign that is opposite to the sign of field curvature induced by the catadioptric objective.

The additional mirrors can have a common axis of rotation (and the beams hit off-axis patches of the reflective surfaces), or common plane of symmetry (and the mirrors are decentered and/or tilted in one plane). Alternatively, the mirrors can have no symmetry at all and be decentered and tilted in three-dimensional space. In some embodiments, angles of incidence of all rays of all beams are not zero to avoid beam obscuration.

In other embodiments, a catadioptric object system can also include optional refractive element(s) between mirrors. To avoid inducing chromatic aberrations, the combined optical power of all surfaces of the refractive elements and the first surface of the monolithic element of the catadioptric objective, for example, surface S6 as shown in FIG. 8, should be close to zero. Here, optical power of a surface is defined as $c*(n'-n)$, where c is surface curvature, and n and n' are indices of refraction from both sides of the surface.

FIGS. 9-12 schematically illustrate exemplary embodiments of catadioptric objective systems that include a catadioptric objective and at least two mirrors to correct the field curvature induced by the catadioptric objective.

Figure 9:
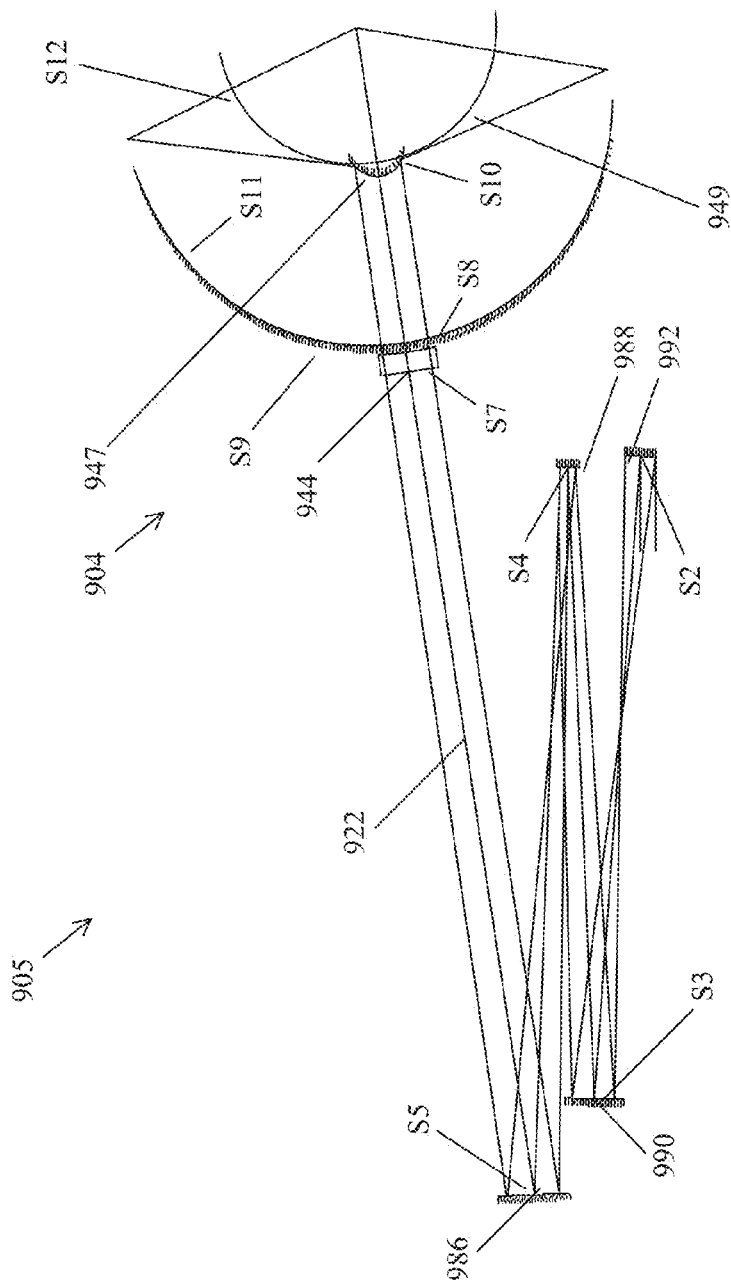
FIG. 9 illustrates an optical schematic of a catadioptric objective system that includes four correcting mirrors.

FIG. 9 schematically illustrates a catadioptric objective system 905 that includes a catadioptric objective 904 (including a refractive element 944 having surfaces S7 and S8) and four mirrors 986, 988, 990, and 992 having reflective surfaces S5, S4, S3, and S2, respectively. No refractive elements are between mirrors 986, 988, 990, and 992. Here, the object can be positioned at a finite distance from the objective or at an infinite distance.

An example prescription for designing the optical surfaces depicted in catadioptric objective system 905 of FIG. 9 is set forth below in Table 3.

TABLE 3

| S# | Surf. type | Radius | Thickness | Material | Mode | De-center |
|---|---|---|---|---|---|---|
| 0 | SPH | 1.00E+18 | 1E+14 | | | |
| 1 | SPH | 1.00E+18 | 4.884033 | | | |
| 2 | AAS | −231.923 | −136.493 | | Reflect | BEN |
| 3 | AAS | 116.3648 | 133.9646 | | Reflect | BEN |
| 4 | AAS | −137.837 | −154.205 | | Reflect | BEN |
| 5 | AAS | 216.1939 | 318.6562 | | Reflect | BEN |
| 7 | SPH | 1.00E+18 | 4 | 'SiO2' | | |
| 8 | ASP | 39.20413 | 1.879349 | | | |
| 9 | ASP | 49.52582 | 36.06278 | 'SiO2' | | |
| 10 | SPH | 5.890262 | −36.0628 | 'SiO2' | Reflect | |
| 11 | ASP | 49.52582 | 38.56278 | 'SiO2' | Reflect | |
| 12 | | 29.34339 | 29.34339 | | | |

Rotationally symmetric aspheric surfaces S8, S9, and S11 can be designed according to Equation 1 defined above. For example, using Equation 1, surfaces S8, S9, and S11 depicted in FIG. 9 can have parameters set forth below in Table 4.

TABLE 4

| Surface # Type | 8 ASP | 9 ASP | 11 ASP |
|---|---|---|---|
| RDY | 39.20413 | 49.52582 | 49.52582 |
| K | 31.33416 | −0.05571 | −0.05571 |
| A | −1.79E−04 | 1.50E−09 | 1.50E−09 |
| B | 5.92E−07 | −9.24E−14 | −9.24E−14 |
| C | −1.67E−08 | 6.23E−16 | 6.23E−16 |
| D | −2.81E−10 | −6.70E−19 | −6.70E−19 |
| E | 0.00E+00 | 4.22E−22 | 4.22E−22 |
| F | 0.00E+00 | −1.34E−25 | −1.34E−25 |
| G | 0.00E+00 | 1.78E−29 | 1.78E−29 |
| H | 0.00E+00 | 0.00E+00 | 0.00E+00 |
| J | 0.00E+00 | 0.00E+00 | 0.00E+00 |

Anamorphic aspheric (AAS) surfaces S4, S5, and S7 can be designed according to the following equation for the sag of the surface parallel to the z-axis:

$$Z(x, y) = \frac{(CUX)x^2 + (CUY)y^2}{1 + \sqrt{1 - (1+KX)(CUX)^2x^2 - (1+KY)(CUY)^2y^2}} + \quad \text{(Eq. 2)}$$

$$AR\{(1-AP)x^2 + (1+AP)y^2\}^2 +$$
$$BR\{(1-BP)x^2 + (1+BP)y^2\}^3 +$$
$$CR\{(1-CP)x^2 + (1+CP)y^2\}^4 +$$
$$DR\{(1-DP)x^2 + (1+DP)y^2\}^5$$

Wherein

CUX and CUY are the curvatures in x and y, respectively;

KX and KY are the conic constants in x and y, respectively, and correspond to eccentricity in the same way as k in Eq. 1;

AR, BR, CR, and DR are the rotationally symmetric portion of the 4th, 6th, 8th, and 10th order deformation from the conic; and AP, BP, CP, and DP are the non-rotationally symmetric components of the 4th, 6th, 8th, and 10th order deformation from the conic.

For example, using Equation 2, surfaces S4, S5, and S7 depicted in FIG. 9 can have parameters set forth below in Table 5.

As shown in FIG. 9, reflective surfaces S2, 23, S4, and S5 of mirrors 992, 990, 988, and 986, respectively, can be decentered. Reflective surfaces S2, 23, S4, and S5 of mirrors 992, 990, 988, and 986 can also be tilted about the x-axis (an axis perpendicular to the plane of the page of FIG. 9). For example, surfaces S2, 23, S4, and S5 can be decentered and tilted according to the parameters set forth in table 6 below.

TABLE 6

| Surface # Type | 2 BEN | 3 BEN | 4 BEN | 5 BEN |
|---|---|---|---|---|
| ADE (in degrees) | −2.09478 | 3.199903 | −2.40523 | 5.551253 |

In one example, the average sum of curvatures of mirrors 986, 988, 990, and 992 is greater than zero, which means mirrors 986, 988, 990, and 992 induce field curvature with a sign opposite to the sign of the field curvature induced by catadioptric objective 904. Accordingly, the field curvature of catadioptric system 905 is corrected or at least reduced.

Figure 10:
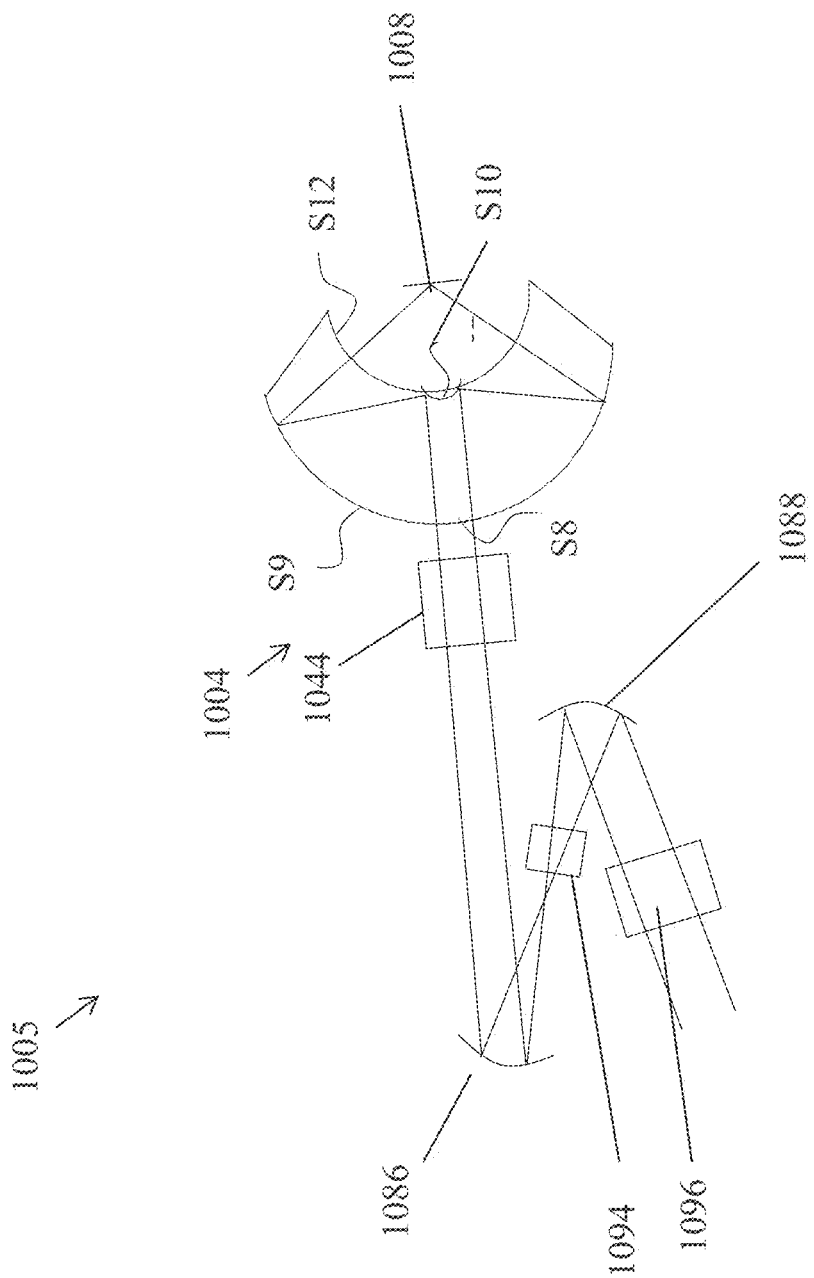
FIG. 10 illustrates an optical schematic of a catadioptric objective system according to another embodiment that includes two correcting mirrors.

FIG. 10 schematically depicts a catadioptric objective system 1005 according to another embodiment. Catadioptric system 1005 includes a catadioptric objective 1004 (including refractive element 1044) and two mirrors 1086 and 1088. Here, the sum of average curvatures of mirrors 1086 and 1088 is greater than zero to correct or reduce the total field curvature induced by catadioptric objective 1004.

In this example, catadioptric objective system 1005 includes refractive element 1094 and refractive element 1096. Refractive element 1094 is positioned between first mirror 1086 and second mirror 1088. Refractive element 1096 is positioned before second mirror 1088. Mirrors 1086 and 1088 can be decentered and tilted.

Figure 11:
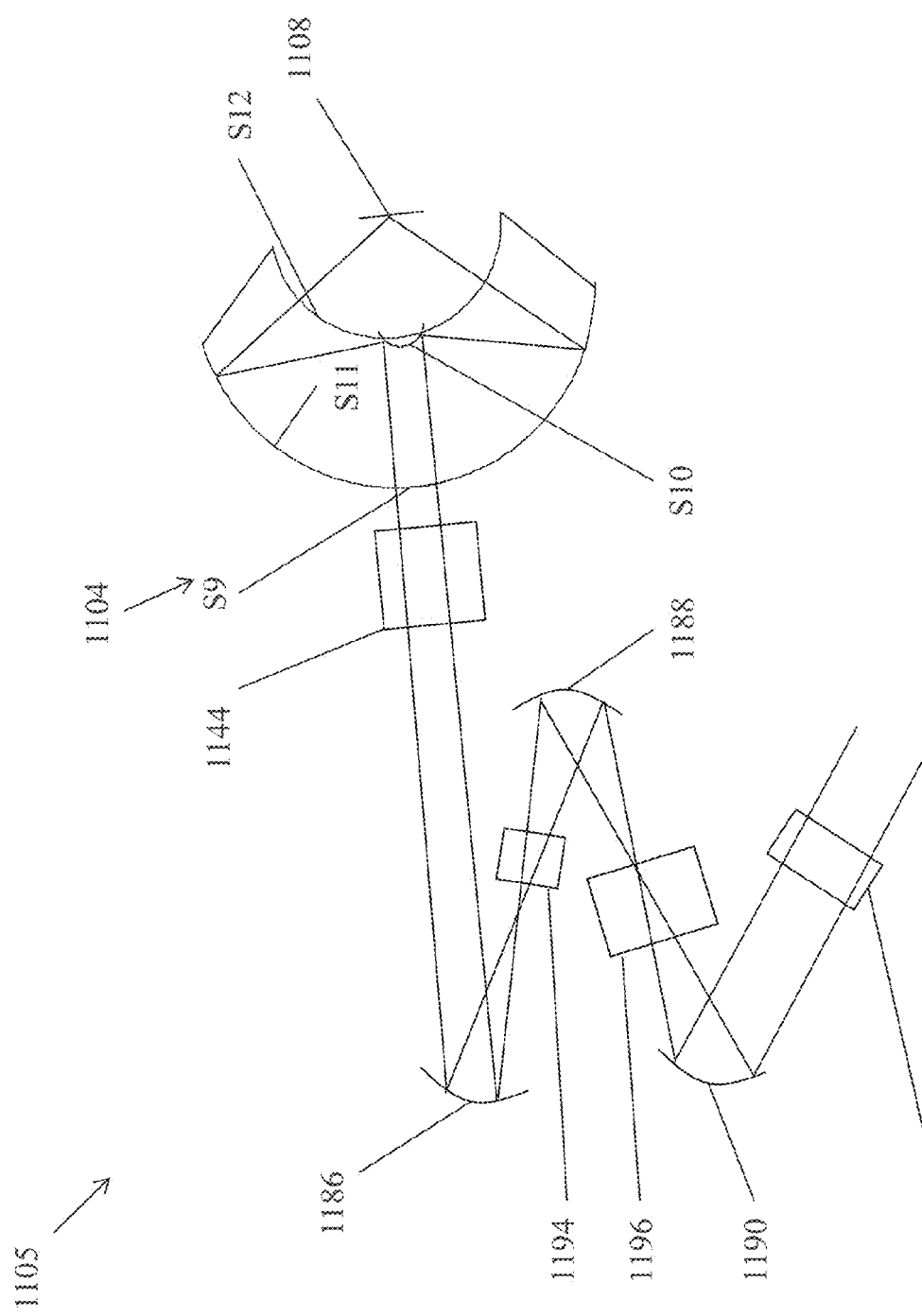
FIG. 11 illustrates an optical schematic of a catadioptric objective system according to yet another embodiment that includes three correcting mirrors.

FIG. 11 schematically depicts a catadioptric objective system 1105 according to another embodiment. Catadioptric system 1105 includes catadioptric objective 1104 (including refractive element 1144) and three mirrors 1186, 1188, and 1190. Mirrors 1186, 1188, and 1190 can be decentered and tilted. The average curvatures of mirrors 1186, 1188, and 1190 are greater than zero. This condition helps correct or reduce field curvature attributable to catadioptric objective 1104.

TABLE 5

| Surface # | 2 | 3 | 4 | 5 |
|---|---|---|---|---|
| X Curvature (CUX) | −0.00432 | 0.008629 | −0.00727 | 0.004663 |
| X Radius | −231.589 | 115.8892 | −137.589 | 214.432 |
| Y Curvature (CUY) | −0.00431 | 0.008594 | −0.00725 | 0.004625 |
| Y Radius | −231.923 | 116.3648 | −137.837 | 216.1939 |
| Y Conic Constant (KY) | 3658.553 | 21.21849 | −186.515 | −110.559 |
| 4th Order Symmetric Coefficient (AR) | 0 | 0 | 0 | 0 |
| 6th Order Symmetric Coefficient (BR) | 0 | 0 | 0 | 0 |
| 8th Order Symmetric Coefficient (CR) | 0 | 0 | 0 | 0 |
| 10th Order Symmetric Coefficient (DR) | 0 | 0 | 0 | 0 |
| X Conic Constant (KX) | 3652.096 | 20.4269 | −185.578 | −107.71 |
| 4th Order Asymmetric Coefficient (AP) | 0 | 0 | 0 | 0 |
| 6th Order Asymmetric Coefficient (BP) | 0 | 0 | 0 | 0 |
| 8th Order Asymmetric Coefficient (CP) | 0 | 0 | 0 | 0 |
| 10th Order Asymmetric Coefficient (DP) | 0 | 0 | 0 | 0 |

In this example, catadioptric objective system 1105 includes refractive element 1194, 1196, and 1198. Refractive element 1194 is positioned in the optical path between mirror 1186 and mirror 1188. Refractive element 1196 is positioned in the optical path between mirror 1190 and mirror 1188. Refractive element 1198 is positioned in the optical path before mirror 1190.

Figure 12:
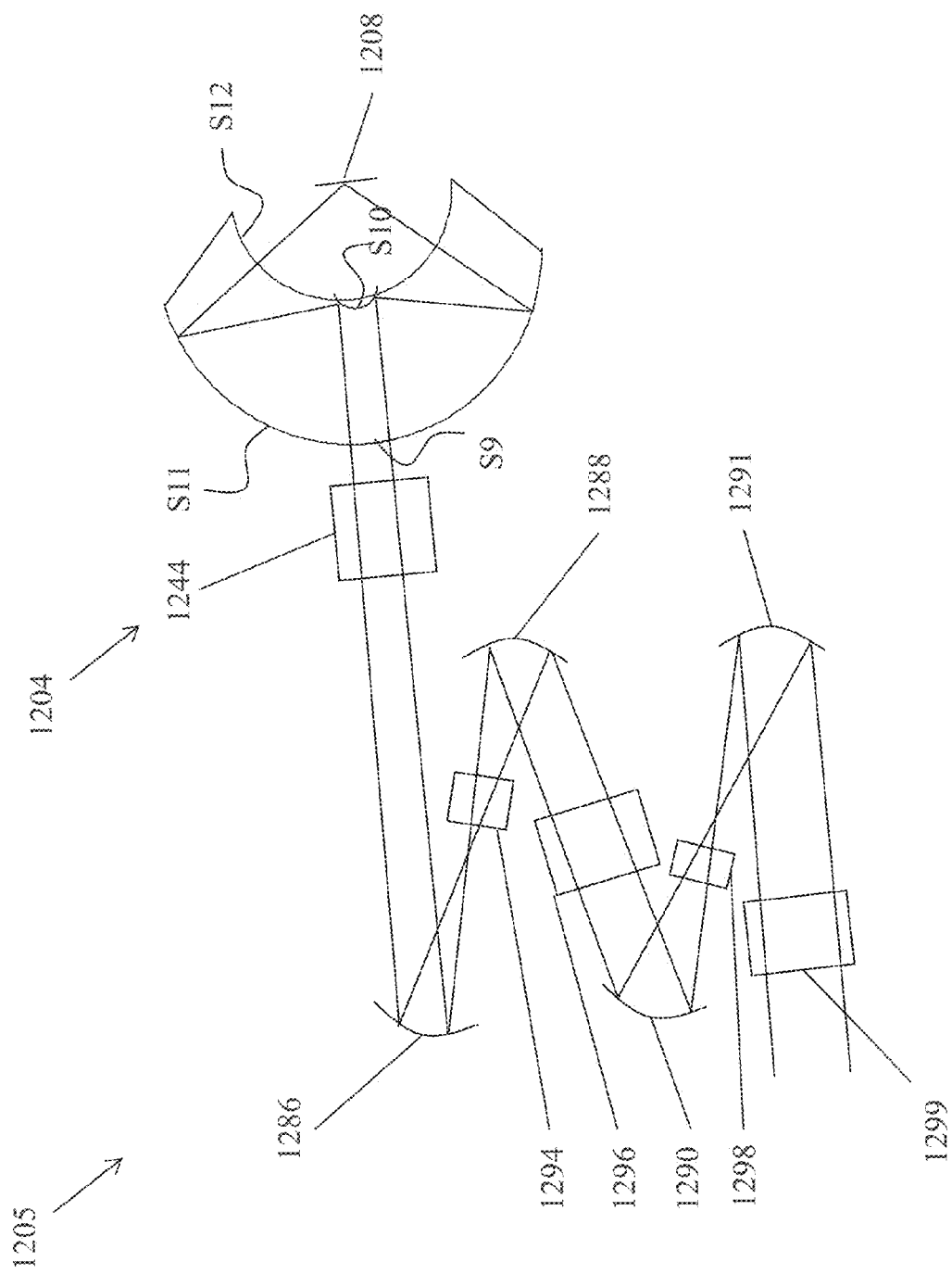
FIG. 12 illustrates an optical schematic of a catadioptric objective according to another embodiment that includes four correcting mirrors and refractive elements.

FIG. 12 depicts a catadioptric objective system 1205 according to an embodiment. Catadioptric system 1205 includes a catadioptric objective 1204 (including refractive element 1244) and for mirrors 1286, 1288, 1290, and 1291. Mirrors 1286, 1288, 1290, and 1291 can be decentered and tilted.

In this example, the average of the curvatures of the reflective surfaces of mirrors 1286, 1288, 1290, and 1291 is greater than zero to correct or reduce the field curvatures induced by catadioptric objective 1204.

Catadioptric objective system 1205 can also include refractive elements 1294, refractive element 1296, refractive element 1298, and refractive element 1299. Refractive element 1294 is positioned in the optical path between mirror 1286 and 1288. Refractive element 1296 is positioned in the optical path between mirror 1290 and mirror 1288. Refractive element 1298 is positioned in the optical path between mirror 1291 and mirror 1290. Refractive element 1299 is positioned in the optical path before mirror 1291.

Example Embodiments of a Refractive Objective

Figure 13:
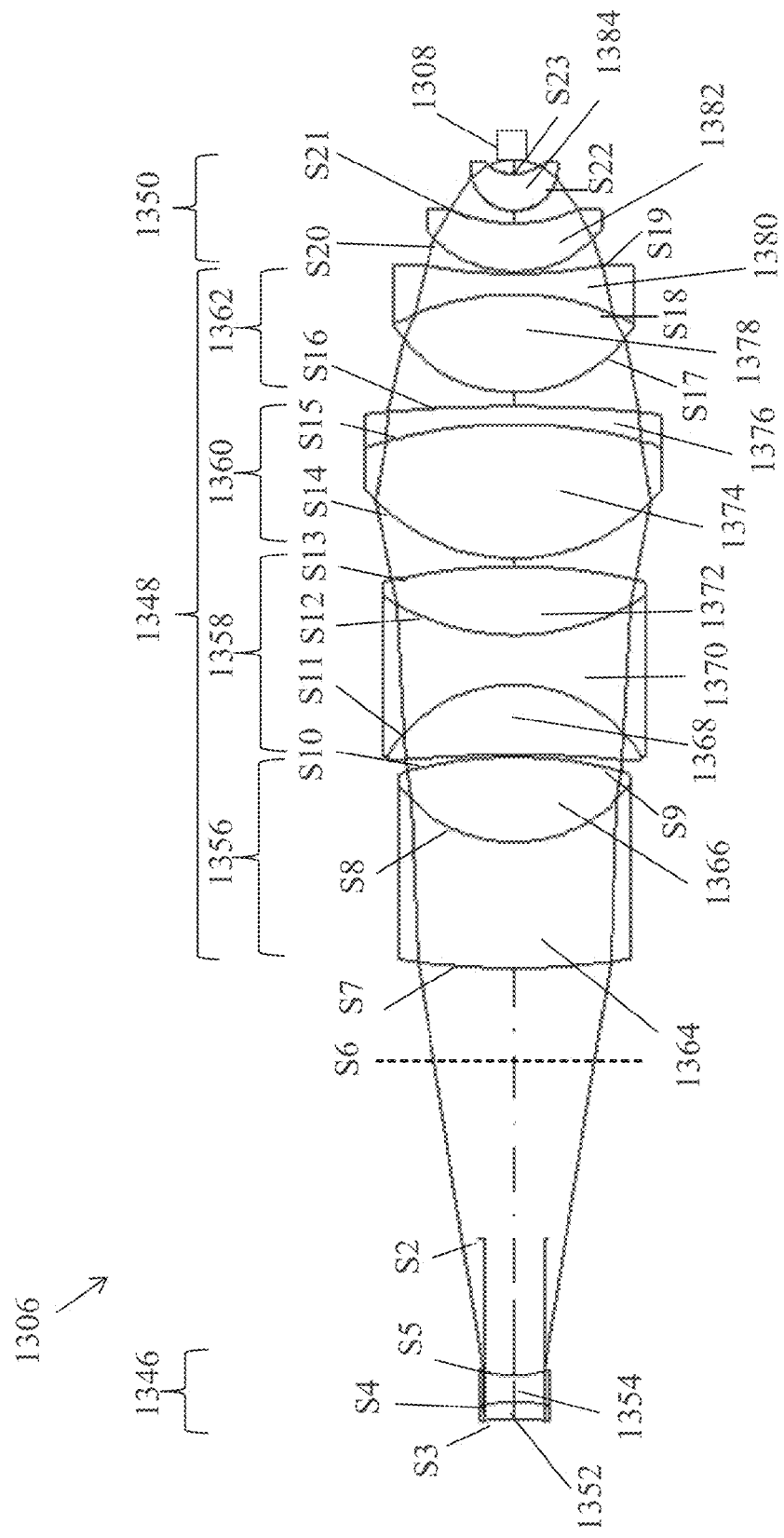
FIG. 13 depicts an optical schematic of a refractive objective.

FIG. 13 schematically illustrates a refractive objective 1306 that can be used with inspection apparatus 500 as shown in FIG. 5. As shown in FIG. 13, refractive objective 1306 includes three lens groups: back lens group 1346, middle lens group 1348, and front lens group 1350. In this example, S2 is an entrance pupil of objective 1306, and S6 is an aperture stop of objective 1306.

In this example, back lens group 1346 includes lens 1352 and lens 1354 forming a doublet. Lens 1352 has a surface S3 and a surface S4. Lens 1354 has surface S4 and a surface S5. Lens 1352 and lens 1354 can form a strong negative doublet for Petzval sum correction.

In this example, middle lens group 1348 includes a doublet 1356, a triplet 1358, a doublet 1360, and a doublet 1362. Doublet 1356 comprises lens 1364 having a surface S7 and a surface S8 and a lens 1366 having a surface S8 and a surface S9. Triplet 1358 includes a lens 1368 having a surface S10 and a surface S11, a lens 1370 having a surface S11 and a surface S12, and a lens 1372 having surface S12 and a surface S13. Doublet 1360 includes a lens 1374 having a surface S14 and a surface S15 and a lens 1376 having surface S15 and a surface S16. Doublet 1362 includes a lens 1378 having a surface S17 and a surface S18 and a lens 1380 having surface S18 and a surface S19.

Regarding triplet 1358, lens 1368 and lens 1372 can be positive lenses, and lens 1370 can be a negative lens. In one embodiment, lens 1372 comprises calcium fluoride ($CaF_2$). Lens 1370 comprises a heavy crown, a heavy flint, a lanthanum flint, or a lanthanum dense flint. Lens 1372 comprises a heavy flint material having an index of refraction that is greater than about 1.75. These combinations of glass materials allow objective 1306 to reach super apochromatic aberration correction.

In this example, front lens group 1350 includes a back meniscus lens 1382 having a surface S20 and a surface S21 and a front meniscus lens 1384 having a surface S22 and a surface S23. Front lens group 1350 decreases the NA from the object space to the entrance of the middle lens group 1348. For example, front lens group 1350 can decrease NA from about 0.95 in the object space to about 0.25-0.4 on the entrance of middle lens group 1348.

In one embodiment, front meniscus lens 1384 comprises a heavy crown material, a heavy flint, a lanthanum flint, or a lanthanum dense flint having an index of refraction greater than about 1.75, for example, about 1.85. In some embodiments, front meniscus lens 1384 comprises a material having an Abbe number that ranges from about 45 to about 50. Back meniscus lens 1382 comprises a heavy flint material having a small Abbe number, for example, an Abbe number less than about 30. Lens 1382 can also have a high index of refraction, for example, about 1.75. In such embodiments, front lens group 1350 can correct or reduce coma and simultaneously do not produce axial color because the difference in the Abbe numbers is large. For example, if front lens 1384 comprises SLAH58_Ohara having an Abbe number of about 44 and back lens 1382 comprises SF6 having an Abbe number of about 27, the difference in Abbe numbers is equal to about 18.

Figure 14:
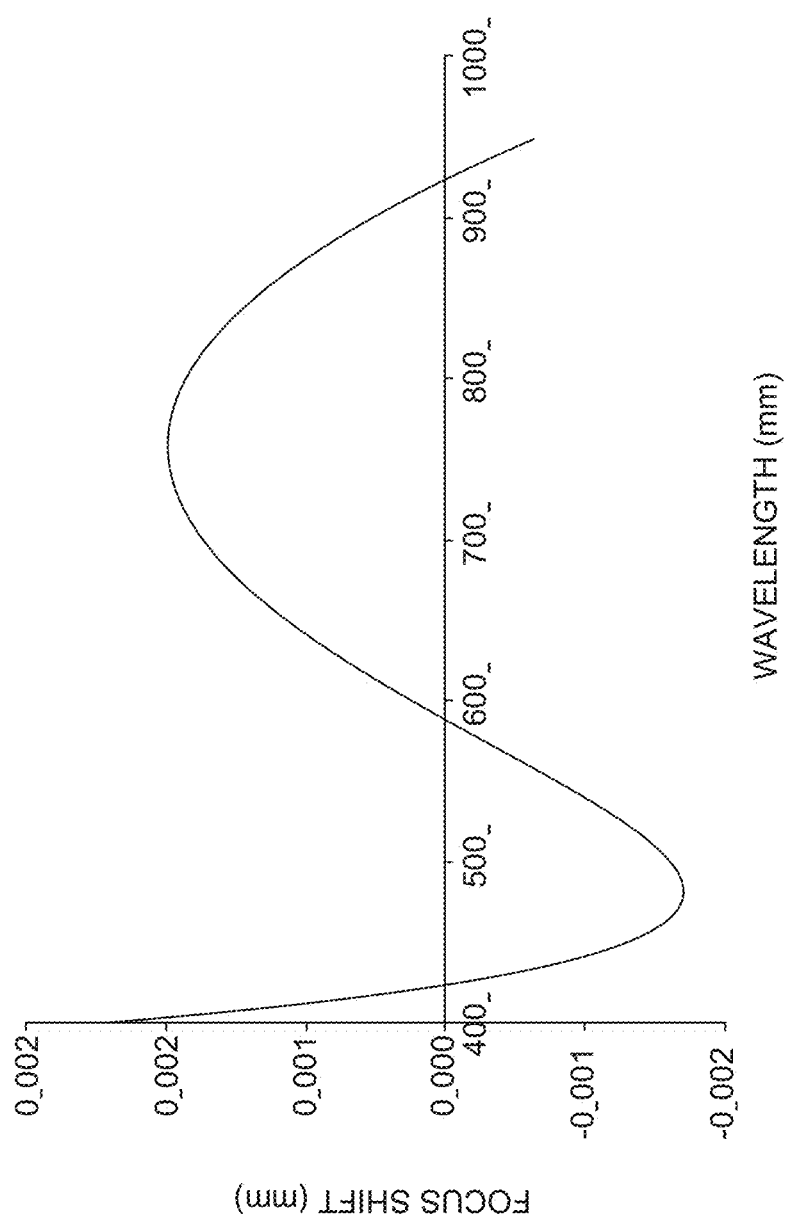
FIG. 14 is a graph showing the longitudinal chromatic aberration of a refractive objective according to an embodiment.

Refractive objectives according to the above described embodiment can have low pupil aberrations and low sensitivity of these aberrations from a target portion of a wafer 1308, which can improve OV measurement accuracy even with moderate wafer stage position accuracy. Additionally, the working distance between the refractive objective and wafer 1308 is improved. In some cases, the working distance is increased about twice that of previous refractive objectives. Further, refractive objectives according to the above described embodiments provide super apochromatic aberration correction. FIG. 14 is a graph showing the longitudinal chromatic aberration of using a refractive objective according to an embodiment. As seen in FIG. 14, the focus shift is zero at three different wavelengths—an improvement over previous refractive objectives.

An example prescription for designing the optical surfaces of refractive objective 1306 depicted in FIG. 13 is set forth below in Table 7.

TABLE 7

| S# | Radius | Thickness | Glass |
| --- | --- | --- | --- |
| 1 | infinity | infinity | |
| 2 | infinity | −20 | |
| 3 | −39.784 | 1.989715 | SF6_SCHOTT |
| 4 | −15.186 | 2.845672 | NFK51A_SCHOTT |
| 5 | 10.786 | 35.24481 | |
| 6 | infinity | 9.994649 | |
| 7 | 83.898 | 14 | NLAK10_SCHOTT |
| 8 | 16.315 | 9.331054 | KGFK70_SUMITA |
| 9 | −46.065 | 0.25 | |
| 10 | −132.997 | 7.814527 | SF6_SCHOTT |
| 11 | −16.390 | 5.5 | LAFN7_SCHOTT |
| 12 | 26.587 | 7.562402 | CAF2_SCHOTT |
| 13 | −65.796 | 0.946029 | |
| 14 | 21.522 | 14.8615 | CAF2_SCHOTT |
| 15 | −54.370 | 2 | NSF57_SCHOTT |
| 16 | −158.282 | 1.564944 | |
| 17 | 15.704 | 10.85286 | CAF2_SCHOTT |
| 18 | −28.913 | 2.272571 | SF6_SCHOTT |
| 19 | 52.739 | 0.25 | |
| 20 | 12.413 | 5.393754 | SF6_SCHOTT |
| 21 | 16.702 | 1.325545 | |
| 22 | 4.865 | 4.080317 | SLAH58_OHARA |
| 23 | 4.605 | 1.919652 | |
| 24 | infinity | 0 | |

Figure 15:
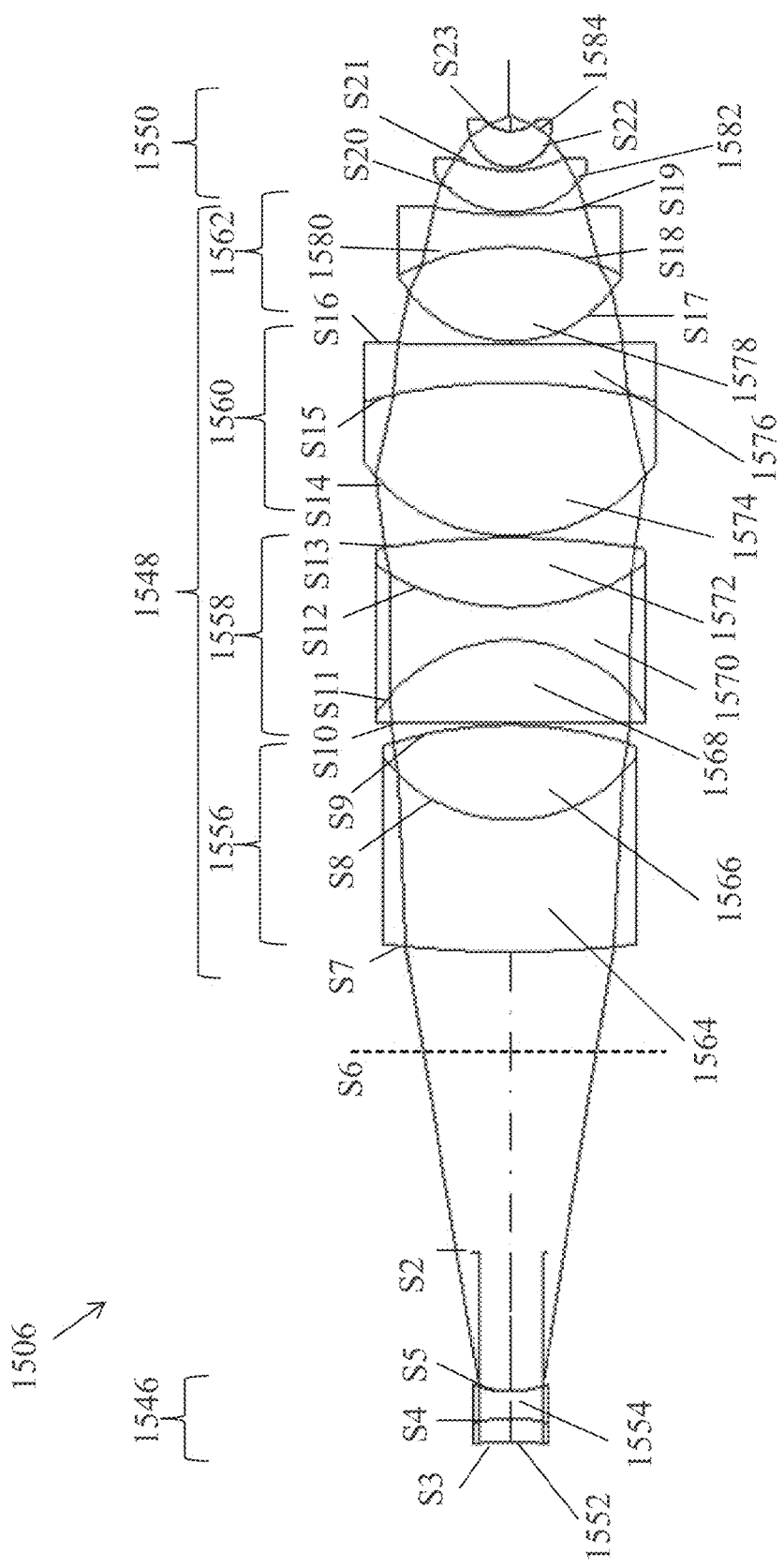
FIG. 15 depicts an optical schematic of a refractive objective according to another embodiment.

FIG. 15 illustrates another embodiment of a refractive objective 1506 that can be used with inspection apparatus 500 as shown in FIG. 5. As shown in FIG. 15, refractive objective 1506 has similar architecture as objective 1306 shown in FIG. 13. However, instead of using lenses comprising $CaF_2$ as in the prescription described in Table 7, objective 1506 uses lenses comprising an artificial crystal fluorite, for example, KCAFK95_SUMITA. Using an artificial crystal fluorite can improve temperature sensitivity of refractive objective 1506, which allows for a wider temperature range during operation and transportation. An example prescription for designing the optical surfaces of refractive objective 1506 depicted in FIG. 15 is set forth below in Table 8.

TABLE 8

| surface | Radius | Thickness | Glass |
| --- | --- | --- | --- |
| 2 | infinity | −20 | |
| 3 | −39.7842 | 2.5 | SF6_SCHOTT |
| 4 | −16.577 | 2.851353 | NFK51A_SCHOTT |
| 5 | 11.27606 | 35.84004 | |
| 6 | infinity | 10.58609 | |
| 7 | 108.0921 | 14 | NLAK10_SCHOTT |
| 8 | 16.96712 | 9.862779 | KGFK70_SUMITA |
| 9 | −42.0926 | 0.25 | |
| 10 | 2525.946 | 8.769319 | SF6_SCHOTT |
| 11 | −16.821 | 3.5 | LAFN7_SCHOTT |
| 12 | 24.73415 | 7.328727 | KCAFK95_SUMITA |
| 13 | −86.3655 | 0.25 | |
| 14 | 19.28516 | 16.1353 | KCAFK95_SUMITA |
| 15 | −61.545 | 4 | NSF57_SCHOTT |
| 16 | 367.0742 | 0.387075 | |
| 17 | 13.47913 | 9.896863 | KCAFK95_SUMITA |
| 18 | −24.9802 | 3.5 | SF6_SCHOTT |
| 19 | 40.69156 | 0.25 | |
| 20 | 9.830512 | 4.364051 | SF6_SCHOTT |
| 21 | 12.95261 | 0.374343 | |
| 22 | 4.403276 | 3.800801 | SLAH58_OHARA |
| 23 | 4.077927 | 1.553261 | |

The refractive and catadioptric objective embodiments discussed above may be used in inspection apparatus 500 depicted in FIG. 5, or in other scatterometers or in any other devices using refractive or catadioptric objectives.

The inspection apparatus 500 as depicted in FIG. 5 may be a stand-alone inspection apparatus or may be incorporated into the lithography apparatus LA or lithographic cell LC of FIGS. 1 and 2, respectively.

Figure 16:
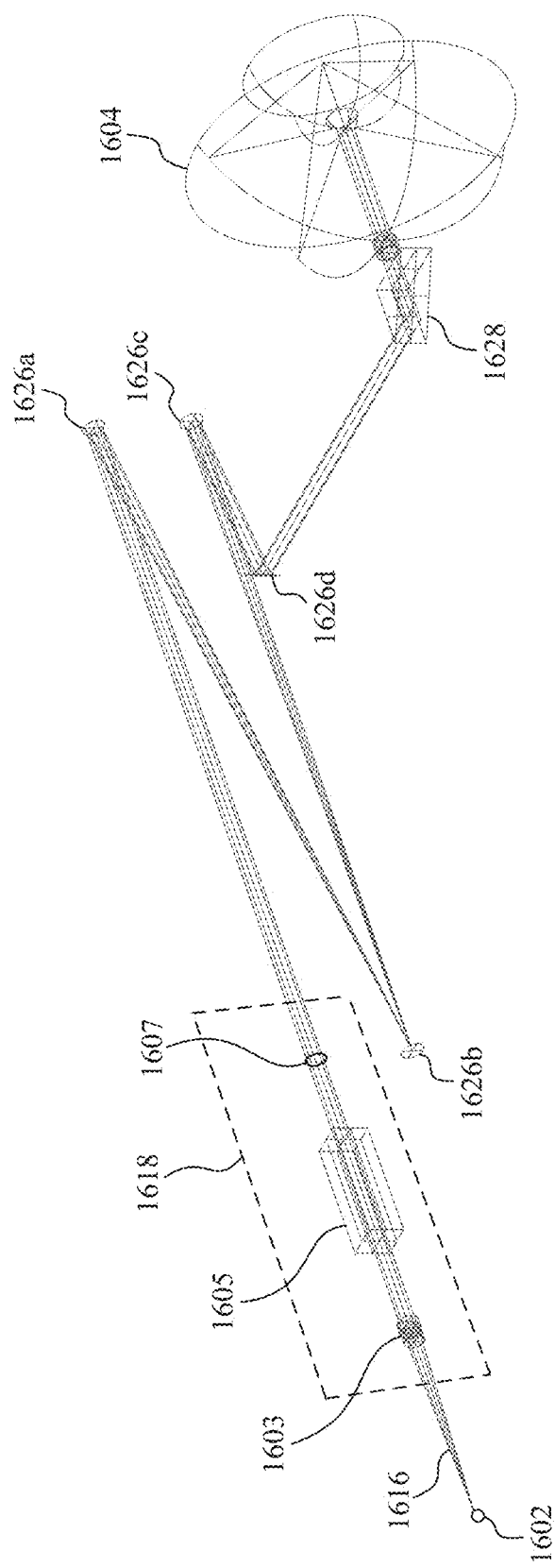
FIG. 16 depicts an optical schematic for an illumination system that can be used with an inspection apparatus according to an embodiment.

FIG. 16 illustrates one embodiment of an illumination system that can be used with an inspection apparatus such as the one illustrated in FIG. 5. As shown in FIG. 16, a radiation source 1602 produces a radiation beam 1616. In some embodiments, radiation source 1602 can be an optical fiber tip. Radiation beam 1616 then passes through an illuminator 1618. In some embodiments, illuminator 1618 includes an achromatic lens doublet 1603, a rotatable polarizer 1605, and a pupil defining aperture 1607. In some embodiments, lens doublet 1603 can be configured to provide chromatic compensation in the broad spectral range from about 200 nm to about 850 nm. In some embodiments, lens doublet 1603 may include a CaF$_2$ lens and a SiO$_2$ lens. Further, in some embodiments, lens doublet 1603 may be positioned along the optical axis and can be adjustable for different discrete wavelengths. In some embodiments, rotatable polarizer 1605 can be a Rochon prism made from MgF$_2$.

After exiting illuminator 1618, a relay mirror optical system can direct the radiation to a catadioptric objective 1604 and a refractive objective (not shown). In some embodiments, as shown in FIG. 16, the relay mirror optical system may include a first spherical relay mirror 1626*a*, a first flat fold mirror 1626*b*, a second spherical relay mirror 1626*c*, and a second flat fold mirror 1626*d*. After second flat fold mirror 1626*d*, the radiation beam passes through a beam splitter 1628 to catadioptric objective 1604.

In some embodiments, pupil aperture 1607 is projected in the plane of the entrance pupils of both catadioptric objective 1604 and the refractive objective by achromatic relay mirrors, for example, first spherical relay mirror 1626*a* and second spherical relay mirror 1626*d*.

Although specific reference may be made in this text to the use of methods and apparatus in the manufacture of ICs, it should be understood that the inspection methods and apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the present invention in the context of optical lithography, it will be appreciated that the present invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the present invention have been described above, it will be appreciated that the present invention may be practiced otherwise than as described. For example, the present invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the present invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An inspection apparatus for optically determining dimensional parameters of a wafer, the inspection apparatus comprising:
   an illumination system configured to receive a first beam and to produce second and third beams therefrom;
   a catadioptric objective configured to direct the second beam to reflect from the wafer;
   a first sensor configured to detect a first image created by the reflected second beam;
   a refractive objective configured to direct the third beam to reflect from the wafer; and
   a second sensor configured to detect a second image created by the reflected third beam,
   wherein the second beam has a first spectral range and the third beam has a second spectral range, which is different than the first spectral range, such that an operating spectral range of the inspection apparatus includes the first and second spectral ranges.

2. The inspection apparatus of claim 1, wherein the illumination system further comprises a beam splitter configured to split the first beam into the second beam and the third beam such that the second beam is configured to provide critical dimension measurements of the wafer and the third beam is configured to provide overlay measurements of the wafer to monitor a lithographic process.

3. The inspection apparatus of claim 1, further comprising, in order from a radiation source:
   a lens doublet configured to be adjustable along an optical axis;
   a rotatable prism polarizer;
   a pupil-defining aperture; and
   a mirror relay optical system configured to image the pupil-defining aperture into a plane of an entrance pupil of the catadioptric objective and into a plane of an entrance pupil of the refractive objective.

4. The inspection apparatus of claim 1, further comprising a beam splitter configured to split the first beam into the second beam and the third beam that are directed to the catadioptric objective and the refractive objective, respectively.

5. The inspection apparatus of claim 1, further comprising a third sensor configured to detect a third image created by the reflected third beam, wherein an overlay dimension measurement of the wafer is determined using the third image.

6. The inspection apparatus of claim 1, wherein the inspection apparatus is configured to determine a first critical dimension measurement of the wafer using the first image and
   wherein the inspection apparatus is configured to determine a second critical dimension measurement using the second image.

7. The inspection apparatus of claim 1, wherein the refractive objective comprises:
   a front lens group having front and back meniscus lenses;
   a middle lens group having a first doublet, a second doublet, a triplet, and a doublet in order from a front to a back of the refractive objective; and
   a back lens group having a negative doublet.

8. The inspection apparatus of claim 7, wherein:
   the triplet of the middle lens group comprises a front positive lens, a middle negative lens, and a back positive lens, and
   the back positive lens comprises a heavy flint.

9. The inspection apparatus of claim 1, further comprising at least two mirrors configured to reduce field curvature induced by the catadioptric objective.

10. The inspection apparatus of claim 9, further comprising a refractive element in an optical path between two mirrors of the at least two mirrors.

11. The inspection apparatus of claim 1, wherein the first spectral range is lower than the second spectral range.

12. The inspection apparatus of claim 11, wherein the first spectral range is about 200 nm to about 425 nm, and wherein the second spectral range is about 425 nm to about 850 nm.

13. A method of determining substrate parameters, the method comprising:
   directing a first beam through a catadioptric objective onto the substrate such that the first beam reflects from the substrate;
   forming a first image of the substrate using the reflected first beam;
   determining a first parameter of the substrate using the first image;
   directing a second beam through a refractive objective onto the substrate such that the second beam reflects from the substrate;
   forming a second image of the substrate using the reflected second beam; and
   determining a second parameter of the substrate using the second image,
   wherein the first beam has a first spectral range and the second beam has a second spectral range, the second spectral range being different than the first spectral range.

14. The method of claim 13, wherein:
   the first parameter is a first critical dimension measurement; and
   the second parameter is a second critical dimension measurement.

15. The method of claim 13, further comprising:
   forming a third image of the substrate using the reflected second beam; and determining a third parameter of the substrate using the third image.

16. The method of claim 13, further comprising:
producing the first and second beams from a third beam,
wherein producing the first and second beams from the third beam comprises splitting the third beam into the first and second beams using a beam splitter.

17. The method of claim 13, wherein the first spectral range is lower than the second spectral range.

18. The method of claim 17, wherein the first spectral range is about 200 nm to about 425 nm, and wherein the second spectral range is about 425 nm to about 850 nm.

19. An inspection apparatus for optically determining dimensional parameters of a wafer, the inspection apparatus comprising:
  an illumination system configured to receive a first beam and to produce second and third beams therefrom;
  a catadioptric objective configured to direct the second beam to reflect from the wafer;
  a first sensor configured to detect a first image created by the reflected second beam;
  a refractive objective configured to direct the third beam to reflect from the wafer;
  a second sensor configured to detect a second image created by the reflected third beam; and
  in order from a radiation source:
    a lens doublet configured to be adjustable along an optical axis;
    a rotatable prism polarizer;
    a pupil-defining aperture; and
    a mirror relay optical system configured to image the pupil-defining aperture into a plane of an entrance pupil of the catadioptric objective and into a plane of an entrance pupil of the refractive objective.

20. An inspection apparatus for optically determining dimensional parameters of a wafer, the inspection apparatus comprising:
  an illumination system configured to receive a first beam and to produce second and third beams therefrom;
  a catadioptric objective configured to direct the second beam to reflect from the wafer;
  a first sensor configured to detect a first image created by the reflected second beam;
  a refractive objective configured to direct the third beam to reflect from the wafer and comprising:
    a front lens group having front and back meniscus lenses,
    a middle lens group having a first doublet, a second doublet, a triplet, and a doublet in order from a front to a back of the refractive objective, and
    a back lens group having a negative doublet; and
  a second sensor configured to detect a second image created by the reflected third beam.

21. The inspection apparatus of claim 20, wherein:
the triplet of the middle lens group comprises a front positive lens, a middle negative lens, and a back positive lens, and
the back positive lens comprises a heavy flint.

* * * * *